United States Patent
Kametani et al.

(10) Patent No.: US 10,441,243 B2
(45) Date of Patent: Oct. 15, 2019

(54) BIOLOGICAL SOUND ANALYZING APPARATUS, BIOLOGICAL SOUND ANALYZING METHOD, COMPUTER PROGRAM, AND RECORDING MEDIUM

(71) Applicant: PIONEER CORPORATION, Tokyo (JP)

(72) Inventors: Ryushin Kametani, Kanagawa (JP); Koichi Ishitoya, Kanagawa (JP); Tomohiro Miura, Kanagawa (JP); Hideyuki Ohkubo, Kanagawa (JP); Tsuyoshi Hasebe, Kanagawa (JP)

(73) Assignee: PIONEER CORPORATION, Tokyo (JP)

( * ) Notice: Subject to any disclaimer, the term of this patent is extended or adjusted under 35 U.S.C. 154(b) by 357 days.

(21) Appl. No.: 15/129,940

(22) PCT Filed: Mar. 28, 2014

(86) PCT No.: PCT/JP2014/059260
§ 371 (c)(1),
(2) Date: Sep. 28, 2016

(87) PCT Pub. No.: WO2015/145754
PCT Pub. Date: Oct. 1, 2015

(65) Prior Publication Data
US 2017/0135670 A1    May 18, 2017

(51) Int. Cl.
*A61B 5/08* (2006.01)
*A61B 7/00* (2006.01)
*A61B 5/00* (2006.01)

(52) U.S. Cl.
CPC .............. *A61B 7/003* (2013.01); *A61B 5/08* (2013.01); *A61B 5/7257* (2013.01);
(Continued)

(58) Field of Classification Search
CPC ......... A61B 7/003; A61B 5/08; A61B 5/7257; A61B 5/7264; A61B 5/7282; A61B 5/7405; A61B 5/742
(Continued)

(56) References Cited

U.S. PATENT DOCUMENTS

| 6,168,568 B1 | 1/2001 | Gavriely |
| 6,261,238 B1 | 7/2001 | Gavriely |

(Continued)

FOREIGN PATENT DOCUMENTS

| JP | 2001-505085 | 4/2001 |
| JP | 2004-357758 | 12/2004 |

(Continued)

OTHER PUBLICATIONS

International Search Report, PCT/JP2014/059260, dated Jun. 17, 2014.
(Continued)

*Primary Examiner* — Navin Natnithithadha
(74) *Attorney, Agent, or Firm* — Young & Thompson

(57) ABSTRACT

A body sound analysis device includes: acquisition means (210, 220) that acquires information relating to a frequency corresponding to a prescribed feature of a spectrum of a body sound; shifting means (230) that shifts, according to the information relating to the frequency, a plurality of reference spectrums that are references for classifying body sounds, and acquires a frequency shift reference spectrum; and output means (240, 250) that outputs a ratio of a plurality of reference spectrums included in the body sounds on the basis of the body sounds and the frequency shift reference spectrum. According to this body sound analysis device, a plurality of types of sounds included in the body sounds can be favorably analyzed.

11 Claims, 17 Drawing Sheets

(52) U.S. Cl.
CPC .......... *A61B 5/7264* (2013.01); *A61B 5/7282* (2013.01); *A61B 5/742* (2013.01); *A61B 5/7405* (2013.01)

(58) Field of Classification Search
USPC .................................................. 600/529–543
See application file for complete search history.

(56) References Cited

U.S. PATENT DOCUMENTS

| | | | |
|---|---|---|---|
| 8,758,262 B2* | 6/2014 | Rhee | A61B 5/113 600/529 |
| 9,109,971 B2 | 8/2015 | Abe et al. | |
| 9,138,199 B2* | 9/2015 | Maskara | A61B 7/003 |
| 9,345,432 B2* | 5/2016 | Salisbury | A61B 5/4818 |
| 2005/0033198 A1* | 2/2005 | Kehyayan | A61B 7/003 600/586 |
| 2006/0198533 A1* | 9/2006 | Wang | A61B 7/00 381/67 |
| 2011/0125044 A1* | 5/2011 | Rhee | A61B 5/113 600/534 |
| 2011/0253739 A1* | 10/2011 | Nishio | B65D 81/3288 222/1 |
| 2012/0150054 A1 | 6/2012 | Abe et al. | |
| 2012/0271199 A1* | 10/2012 | Salisbury | A61B 5/4818 600/586 |
| 2013/0178756 A1* | 7/2013 | Suzuki | A61B 5/0826 600/529 |
| 2014/0155762 A1* | 6/2014 | Maskara | A61B 7/003 600/484 |
| 2017/0135649 A1* | 5/2017 | Kametani | A61B 5/0826 |

FOREIGN PATENT DOCUMENTS

| | | |
|---|---|---|
| JP | 2012-120688 | 6/2012 |
| JP | 2013-123495 | 6/2013 |

OTHER PUBLICATIONS

Tomoya Sakai, "Extraction of Abnormal Lung Sounds via Sparse Representation", IEICE Technical Report, 2011, vol. 111, No. 27, pp. 131 to 136.

* cited by examiner

FIG. 21
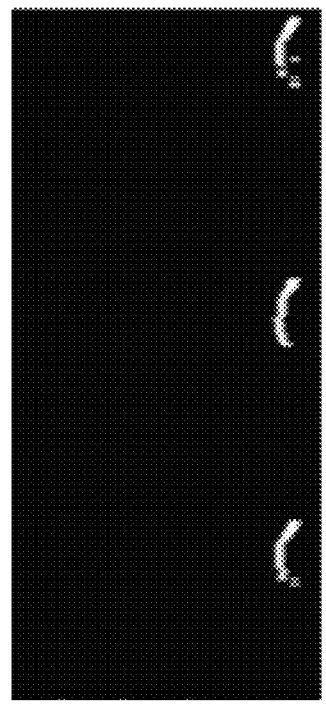
Frequency analysis image
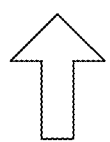
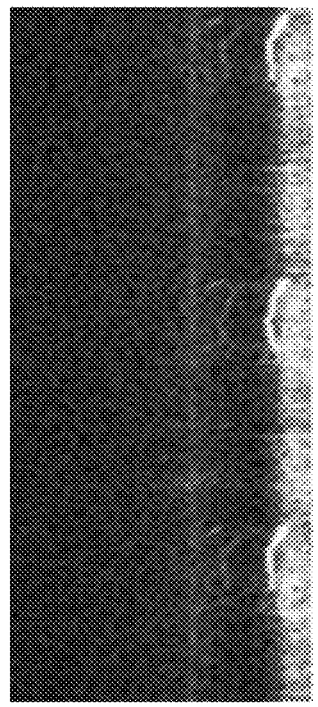
Extracted image

BIOLOGICAL SOUND ANALYZING APPARATUS, BIOLOGICAL SOUND ANALYZING METHOD, COMPUTER PROGRAM, AND RECORDING MEDIUM

TECHNICAL FIELD

The present invention relates to a biological sound analyzing apparatus and a biological sound analyzing method for analyzing biological sounds, such as, for example, breath sounds, a computer program, and a recording medium.

BACKGROUND ART

For this type of apparatus, there is known an apparatus configured to distinguish between normal breath sounds and abnormal breath sounds, regarding breath sounds detected by an electronic stethoscope or the like. For example, in Patent Literature 1, there is proposed a method of dividing sounds into normal breath sounds and continuous pulmonary adventitious sounds on the basis of local variance values on a spectrum. In Patent Literature 2, there is proposed a method of determining the degree of abnormality of a respiratory state on the basis of the degree of correlation with a preset model. In Patent Literature 3, there is proposed a method of approximating a spectrum shape by using a mixture Gaussian distribution and determining an abnormal breath sound type.

CITATION LIST

Patent Literature

Patent Literature 1: Japanese Patent Application Laid Open No. 2004-357758
Patent Literature 2: Japanese Patent Application Laid Open No. 2012-120688
Patent Literature 3: Japanese Patent Application Laid Open No. 2013-123495

SUMMARY OF INVENTION

Technical Problem

In the technologies described in the Patent Literatures 1 to 3 described above, however, if a plurality of abnormal breath sounds are mixedly heard (in particular, if the plurality of abnormal breath sounds overlap on the same frequency axis), it is hard to divide and detect the abnormal breath sounds, which is technically problematic.

Problems to be solved by the present invention include the aforementioned technical problem as one example. It is therefore an object of the present invention to provide a biological sound analyzing apparatus and a biological sound analyzing method in which a plurality of sound types included in biological sounds can be preferably analyzed, a computer program, and a recording medium.

Solution to Problem

The above object of the present invention can be achieved by a biological sound analyzing apparatus comprising: an obtaining device configured to obtain information regarding frequency corresponding to predetermined characteristics of a spectrum of biological sounds; a shifting device configured to shift a plurality of reference spectra, which are references for classifying the biological sounds, in accordance with the information regarding the frequency, and configured to obtain frequency-shifted reference spectra; and an outputting device configured to output a ratio of each of the plurality of reference spectra included in the biological sounds on the basis of the biological sounds and the frequency-shifted reference spectra.

The above object of the present invention can be achieved by a biological sound analyzing method comprising: an obtaining process of obtaining information regarding frequency corresponding to predetermined characteristics of a spectrum of biological sounds; a shifting process of shifting a plurality of reference spectra, which are references for classifying the biological sounds, in accordance with the information regarding the frequency, and obtaining frequency-shifted reference spectra; and an outputting process of outputting a ratio of each of the plurality of reference spectra included in the biological sounds on the basis of the biological sounds and the frequency-shifted reference spectra.

The above object of the present invention can be achieved by a computer program product for making a computer perform: an obtaining process of obtaining information regarding frequency corresponding to predetermined characteristics of a spectrum of biological sounds; a shifting process of shifting a plurality of reference spectra, which are references for classifying the biological sounds, in accordance with the information regarding the frequency, and obtaining frequency-shifted reference spectra; and an outputting process of outputting a ratio of each of the plurality of reference spectra included in the biological sounds on the basis of the biological sounds and the frequency-shifted reference spectra.

The above object of the present invention can be achieved by a recording medium on which the computer program product described above is recorded.

BRIEF DESCRIPTION OF DRAWINGS

FIG. 21 is a spectrogram illustrating an example of extraction of wheezes.

DESCRIPTION OF EMBODIMENTS

<1>

Figure 1:
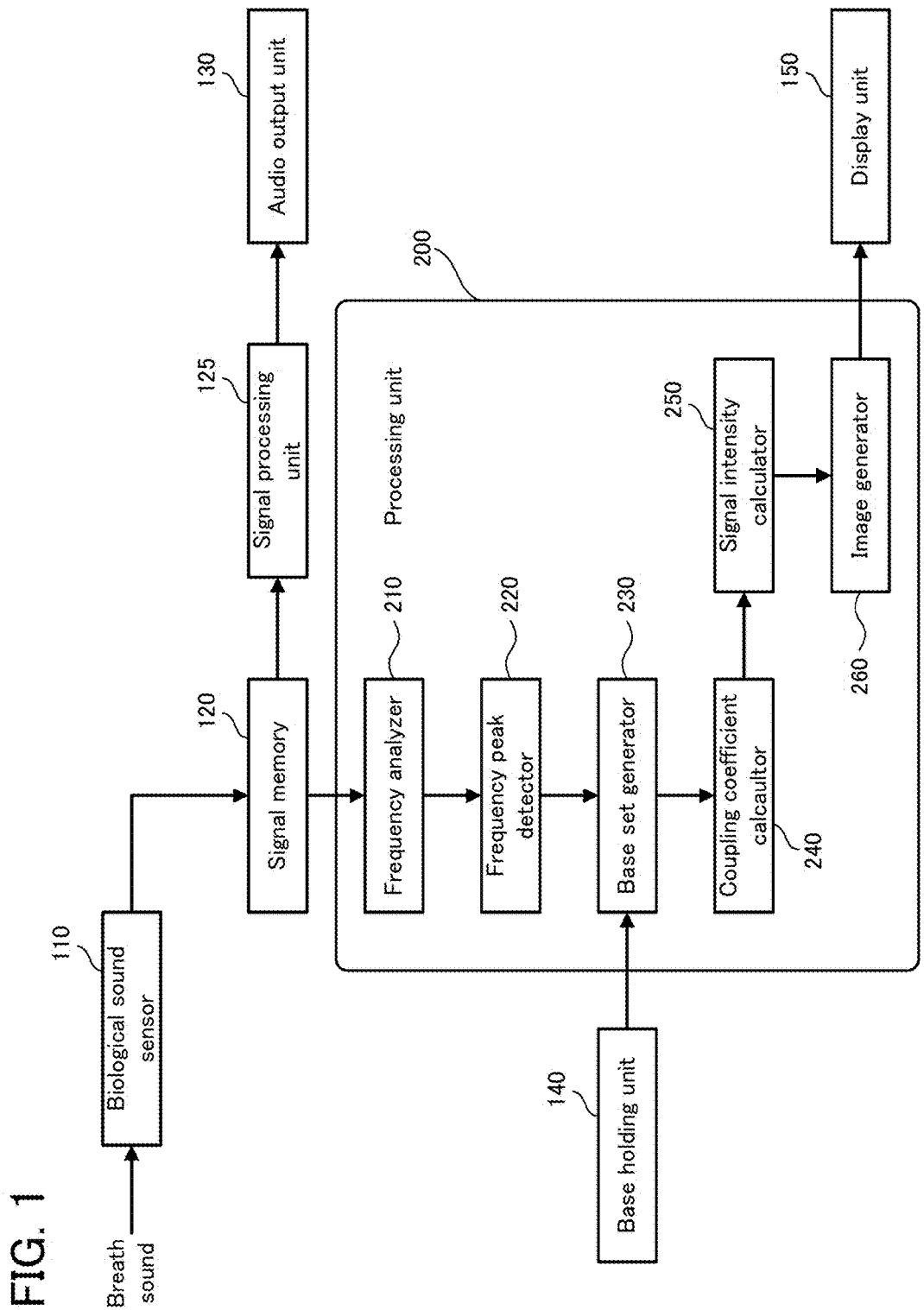
FIG. 1 is a block diagram illustrating an entire configuration of a biological sound analyzing apparatus according to an example.

A biological sound analyzing apparatus according to an embodiment provide with: an obtaining device configured to obtain information regarding frequency corresponding to predetermined characteristics of a spectrum of biological sounds; a shifting device configured to shift a plurality of reference spectra, which are references for classifying the biological sounds, in accordance with the information regarding the frequency, and configured to obtain frequency-shifted reference spectra; and an outputting device configured to output a ratio of each of the plurality of reference spectra included in the biological sounds on the basis of the biological sounds and the frequency-shifted reference spectra.

According to the biological sound analyzing apparatus in the embodiment, in its operation, the information regarding the frequency corresponding to the predetermined characteristics of the spectrum of biological sounds is firstly obtained. The "biological sounds" herein mean sounds generated from a living body, such as breath sounds, heartbeat sounds, and bowel sounds. Moreover, the "predetermined characteristics" mean characteristics generated at particular frequencies in accordance with sound types included in the spectrum of biological sounds, and are, for example, a peak(s) that appears in frequency-analyzed signals, or the like. Moreover, the "information regarding the frequency" is not limited to information directly indicating the frequency, but may include information from which the frequency can be derived.

If the information regarding the frequency is obtained, the plurality of reference spectra, which are references for classifying the biological sounds, are shifted in accordance with the information regarding the frequency, and the frequency-shifted reference spectra are obtained. The "reference spectra" herein are spectra set in advance in accordance with respective sounds types in order to classify the plurality of sound types included in the biological sounds (e.g. normal breath sounds, continuous pulmonary adventitious sounds, fine crackles, etc.). The reference spectra are frequency-shifted in accordance with, for example, a position(s) of the peak(s) or the like, which are the predetermined characteristics obtained from the biological sounds, to make the frequency-shifted reference spectra.

If the frequency-shifted reference spectra are obtained, the ratio of each of the plurality of reference spectra included in the biological sounds is outputted on the basis of the biological sounds and the frequency-shifted reference spectra. Specifically, it is calculated in what rate the sound types corresponding to the plurality of reference spectra are included in the biological sounds, which are to be analyzed, and a result of the calculation is outputted. More specifically, for example, arithmetic operation using the plurality of reference spectra as bases is performed on the spectrum of the biological sounds, thereby to calculate the ratio of each of the reference spectra as a coupling coefficient.

As a result, according to the biological sound analyzing apparatus in the embodiment, the biological sounds including the plurality of sound types can be preferably analyzed. Particularly in the embodiment, even if the plurality of sound types are mixed on the same frequency axis, the ratio of each sound type can be preferably analyzed.

<2>

In one aspect of the biological sound analyzing apparatus according to the embodiment, wherein the biological sounds are breath sounds.

According to this aspect, the ratio of each of the plurality of sound types included in the breath sounds (specifically, normal breath sounds and abnormal breath sounds, such as continuous pulmonary adventitious sounds and fine crackles, etc.) can be preferably analyzed. By this, for example, if a health condition is diagnosed from the breath sounds or in similar cases, more objective and accurate diagnoses can be made. Specifically, more accurate diagnoses can be made in comparison with a case where the presence or absence of abnormal breath sounds is diagnosed only from the breath sounds that are heard through a stethoscope or the like. Particularly in this aspect, there is no need to use the technology for distinguishing between the mixed plurality types of breath sounds, and the breath sounds can be extremely preferably analyzed regardless of a user's skill. More specifically, for example, not only a skillful doctor but also an inexperienced doctor or nurse can appropriately distinguish abnormal breath sounds.

<3>

In the aforementioned aspect in which the breath sounds are analyzed, the plurality of reference spectra may include reference spectra corresponding to adventitious sounds.

In this case, a ratio of the adventitious sounds included in the breath sounds (i.e. abnormal breath sounds) is outputted, and the health condition can be preferably diagnosed. The reference spectra may include reference spectra corresponding to a plurality of types of adventitious sounds, or may include reference spectra corresponding to sound types other than the adventitious sounds.

<4>

In another aspect of the biological sound analyzing apparatus according to the embodiment, wherein the predetermined characteristics is a local maximum value.

According to this aspect, frequency analysis, such as Fast Fourier Transform (FFT), is performed, for example, on signals indicating the biological sounds. Then, the information regarding the frequency corresponding to the local maximum value (i.e. peak(s)) of the analysis result is obtained. The information regarding the frequency is obtained as what corresponds to a position of the local maximum value. The information regarding the frequency may be obtained as information regarding frequency corresponding to a nearby position of the local maximum value, even though it is not the frequency that completely matches the position of the local maximum value.

As described above, by using the local maximum value as the predetermined characteristics of the spectrum of the biological sounds, it is possible to obtain the information regarding the frequency, more easily and accurately.

<5>

In another aspect of the biological sound analyzing apparatus according to the embodiment, wherein said outputting device uses non-negative approximation to calculate the ratio of each of the plurality of reference spectra.

According to this aspect, the non-negative approximation (i.e. approximation in which the coupling coefficient is not negative) is used when the ratio of each of the plurality of reference spectra is calculated. As the non-negative approximation, for example, Non-negative Matrix Factorization (NMF) is exemplified.

Here, if approximation that is not non-negative (i.e. approximation in which the coupling coefficient could be negative) is used, the ratio obtained by arithmetic operation is possibly not a value that indicates the ratio of each reference spectrum. In other words, even if the approximation is appropriately performed, an inappropriate value is possibly calculated for a value indicating a component amount of each reference spectrum.

In contrast, the value indicating the component amount of each reference spectrum can be preferably calculated by using the aforementioned non-negative approximation.

<6>

In another aspect of the biological sound analyzing apparatus according to the embodiment, further comprising a separating device configured to separate and output the spectrum of the biological sounds into a plurality of spectra corresponding to the plurality of reference spectra.

According to this aspect, the spectrum of the biological sounds is separated into the plurality of spectra corresponding to the plurality of reference spectra, which are then outputted. Thus, for example, if the breath sounds are analyzed, normal breath sounds and abnormal breath sounds can be separately outputted. The separated plurality of spectra can be separately outputted, for example, as a plurality of audio data. Alternatively, the separated plurality of spectra may be also separately outputted as a plurality of image data (e.g. images indicating spectra).

<7>

A biological sound analyzing method according to an embodiment provide with: an obtaining process of obtaining information regarding frequency corresponding to predetermined characteristics of a spectrum of biological sounds; a shifting process of shifting a plurality of reference spectra, which are references for classifying the biological sounds, in accordance with the information regarding the frequency, and obtaining frequency-shifted reference spectra; and an outputting process of outputting a ratio of each of the plurality of reference spectra included in the biological sounds on the basis of the biological sounds and the frequency-shifted reference spectra.

According to the biological sound analyzing method in the embodiment, the biological sounds including the plurality of sound types can be preferably analyzed, as in the biological sound analyzing apparatus in the embodiment described above.

Even the biological sound analyzing method in the embodiment can also adopt the same various aspects as those of the biological sound analyzing apparatus in the embodiment described above.

<8>

A computer program product according to an embodiment for making a computer perform: an obtaining process of obtaining information regarding frequency corresponding to predetermined characteristics of a spectrum of biological sounds; a shifting process of shifting a plurality of reference spectra, which are references for classifying the biological sounds, in accordance with the information regarding the frequency, and obtaining frequency-shifted reference spectra; and an outputting process of outputting a ratio of each of the plurality of reference spectra included in the biological sounds on the basis of the biological sounds and the frequency-shifted reference spectra.

According to the computer program in the embodiment, it can make a computer to perform the same processes as those in the biological sound analyzing method in the embodiment described above. Therefore, the biological sounds including the plurality of sound types can be preferably analyzed.

Even the computer program in the embodiment can also adopt the same various aspects as those of the biological sound analyzing apparatus in the embodiment described above.

<9>

On a recording medium according to an embodiment, the computer program product described above is recorded.

According to the recording medium in the embodiment, the biological sounds including the plurality of sound types can be preferably analyzed by making a computer perform the computer program described above.

The operation and other advantages of the biological analyzing apparatus, the biological analyzing method, the computer program, and the recording medium according to the embodiments will be explained in more detail in the following examples.

EXAMPLES

Hereinafter, a biological analyzing apparatus, a biological analyzing method, a computer program, and a recording medium according to examples will be explained in detail. In the following example, an explanation is given for a case where the biological analyzing apparatus according to the present invention is applied to an apparatus configured to analyze breath sounds of a living body.

<Entire Configuration>

Firstly, an entire configuration of the biological analyzing apparatus according to the example will be explained with reference to FIG. 1. FIG. 1 is a block diagram illustrating the entire configuration of the biological sound analyzing apparatus according to the example.

In FIG. 1, the biological sound analyzing apparatus according to the example is provided with a biological sound sensor 110, a signal memory 120, a signal processing unit 125, an audio output unit 130, a basis holding unit 140, a display unit 150, and a processing unit 200, as main components.

The biological sound sensor 110 is a sensor configured to detect breath sounds of a living body. The biological sound sensor 110 is provided, for example, with a microphone using an electrets condenser microphone (ECM) and a piezoelectric microphone, a vibration sensor, and the like.

The signal memory 120 is configured as a buffer, such as, for example, a random access memory (RAM), and is configured to temporarily store signals indicating the breath sounds detected on the biological sound sensor 110 (hereinafter referred to as "breath sound signals" as occasion demands). The signal memory 120 is configured to output the stored signals to each of the audio output unit 130 and the processing unit 200.

The signal processing unit 125 is configured to process the sounds obtained on the biological sound sensor 110 and output them to the audio output unit 130. The signal processing unit 125 functions, for example, as an equalizer and a filter, and is configured to process the obtained sounds in an easy-to-listen state for a person.

The audio output unit 130 is configured, for example, as a speaker and a headphone, and is configured to output the breath sounds, which are detected on the biological sound sensor 110 and which are processed on the signal processing unit 125.

The basis holding unit 140 is configured, for example, as a read only memory (ROM) or the like, and is configured to store therein bases corresponding to predetermined sound types that can be included in the breath sounds. The basis according to the example is one example of the "reference spectrum" according to the present invention.

The display unit 150 is configured as a display, such as, for example, a liquid crystal monitor, and is configured to display image data outputted from the processing unit 200.

The processing unit 200 includes a plurality of arithmetic circuits and memories and the like. The processing unit 200 is provided with a frequency analyzer 210, a frequency peak detector 220, a basis set generator 230, a coupling coefficient calculator 240, a signal intensity calculator 250, and an image generator 260.

Respective operations of the parts of the processing unit 200 will be detailed later.

<Explanation of Operations>

Figure 2:
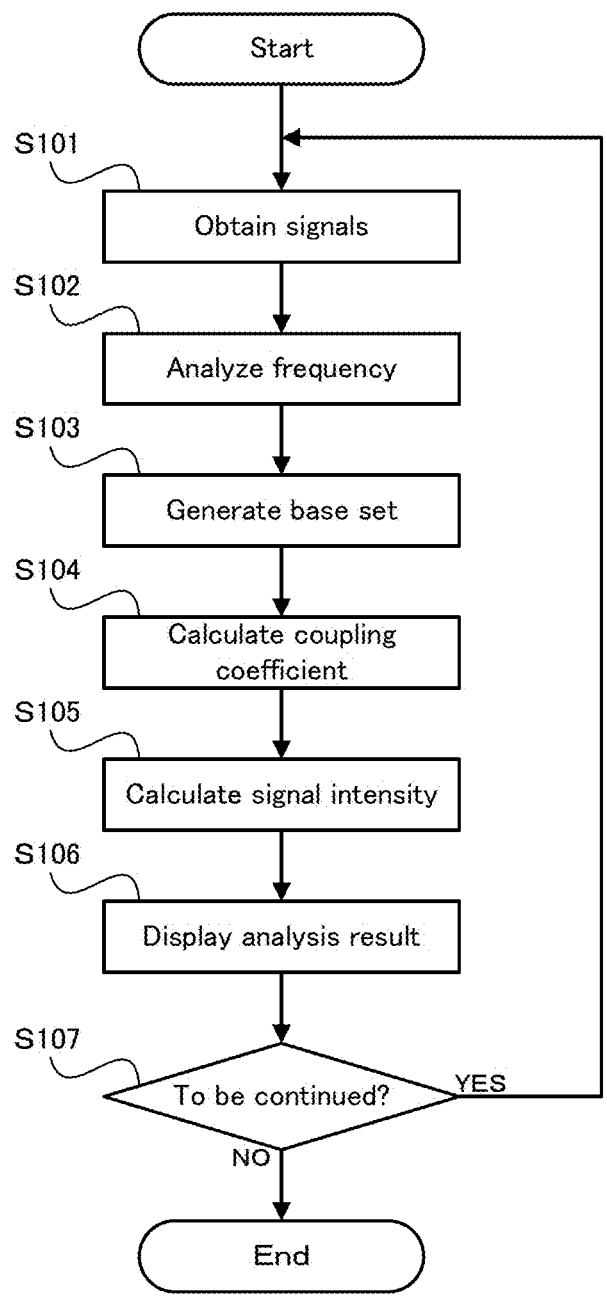
FIG. 2 is a flowchart illustrating operations of the biological sound analyzing apparatus according to the example.

Next, the operations of the biological sound analyzing apparatus according to the example will be explained with reference to FIG. 2. FIG. 2 is a flowchart illustrating the operations of the biological sound analyzing apparatus according to the example. Here, a simple explanation will be given in order to understand an entire flow of processes performed by the biological sound analyzing apparatus according to the example. The details of each process will be described later.

In FIG. 2, in operation of the biological sound analyzing apparatus according to the example, firstly, breath sounds are detected on the biological sound sensor 110 and breath sound signals are obtained by the processing unit 200 (step S101).

If the breath sound signals are obtained, frequency analysis (e.g. Fast Fourier Transform) is performed on the frequency analyzer 210 (step S102). Moreover, peaks (i.e. the local maximum value according to the embodiment) are detected by using a frequency analysis result on the frequency peak detector 220.

Then, a basis set is generated on the basis set generator 230 (step S103). Specifically, the basis set generator 230 generates the basis set by using the bases stored in the basis holding unit 140. At this time, the basis set generator 230 shifts the bases on the basis of positions of the peaks (i.e. the corresponding frequency according to the embodiment) obtained from the frequency analysis result.

If the basis set is generated, a coupling coefficient is calculated on the coupling coefficient calculator 240 on the basis of the frequency analysis result and the basis set (step S104).

If the coupling coefficient is calculated, signal intensity according to the coupling coefficient is calculated on the signal intensity calculator 250 (step S105). In other words, a ratio of each sound type included in the breath sound signals is calculated.

If the signal intensity is calculated, image data indicating the signal intensity is generated on the image generator 260. The generated image data is displayed as an analysis result on the display unit 150 (step S106).

Then, it is determined whether or not the analysis process is to be continued (step S107). If it is determined that the analysis process is to be continued (the step S107: YES), the process from the step S101 is performed again. If it is determined that the analysis process is not to be continued (the step S107: NO), a series of process operations is ended.

<Specific Examples of Breath Sound Signals>

Figure 3:
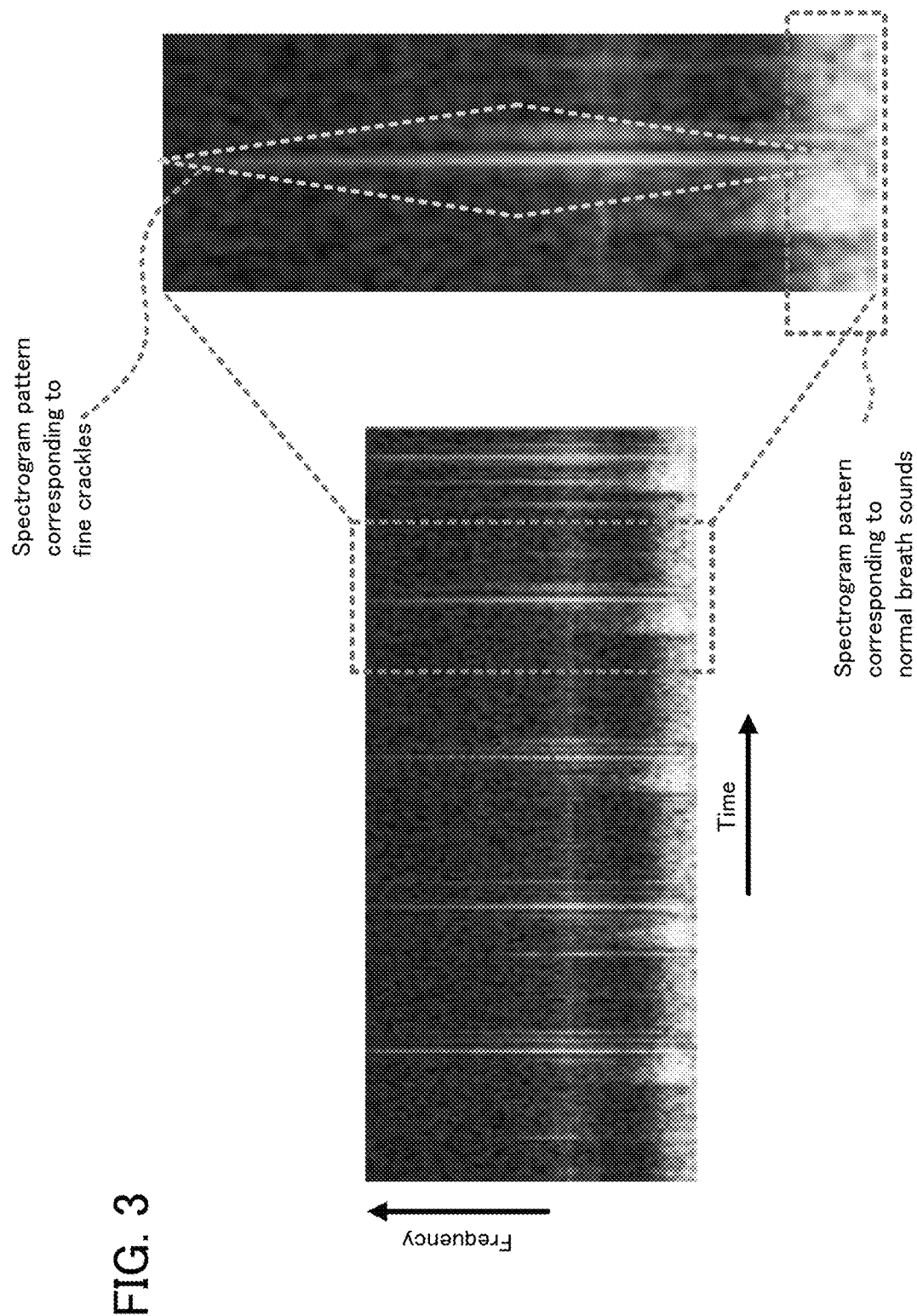
FIG. 3 is a spectrogram illustrating a frequency analysis result of breath sounds including fine crackles.
Figure 4:
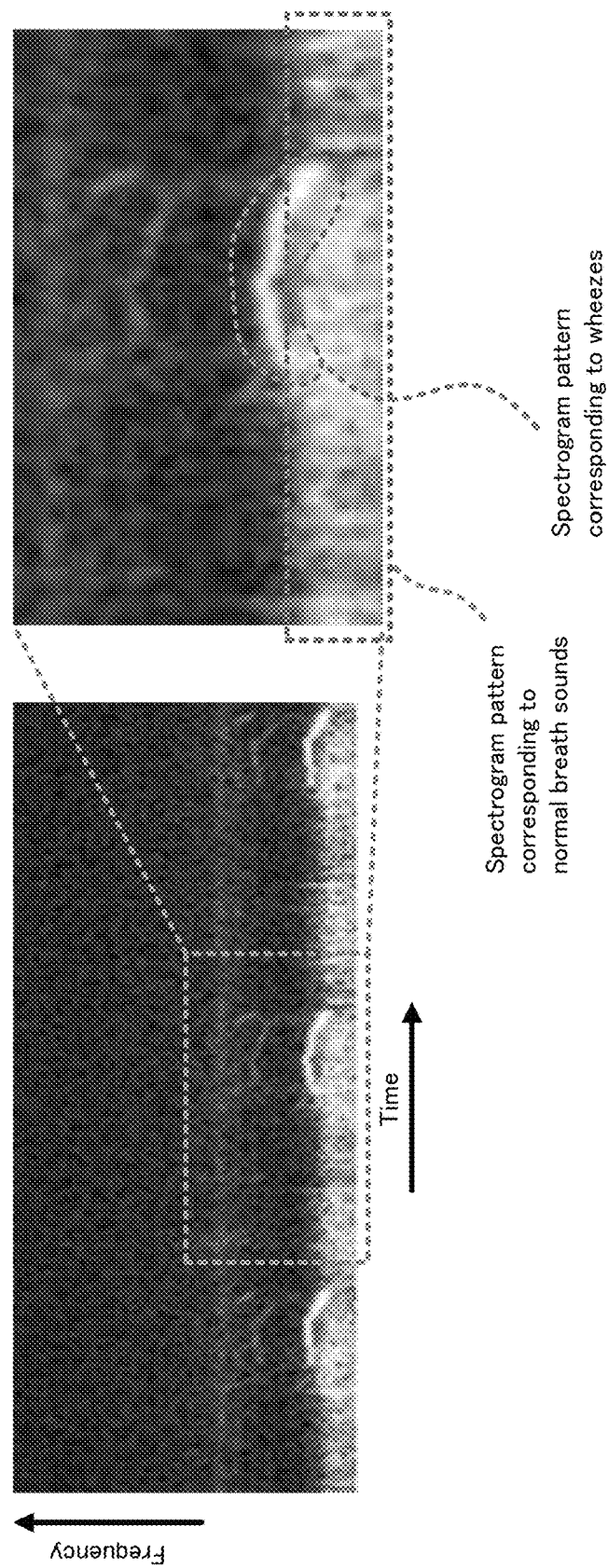
FIG. 4 is a spectrogram illustrating a frequency analysis result of breath sounds including wheezes.

Next, specific examples of the breath sound signals analyzed on the biological sound analyzing apparatus according to the example will be explained with reference to FIG. 3 and FIG. 4. FIG. 3 is a spectrogram illustrating a frequency analysis result of breath sounds including fine crackles. FIG. 4 is a spectrogram illustrating a frequency analysis result of breath sounds including wheezes.

In the example illustrated in FIG. 3, in addition to a spectrogram pattern corresponding to normal breath sounds, a spectrogram pattern corresponding to fine crackles, which is one of the abnormal breath sounds, is also observed. The spectrogram pattern corresponding to fine crackle has a shape close to a rhombus, as illustrated in an enlarged part in FIG. 3.

In the example illustrated in FIG. 4, in addition to a spectrogram pattern corresponding to normal breath sounds, a spectrogram pattern corresponding to wheezes, which is one of the abnormal breath sounds, is also observed. The spectrogram pattern corresponding to wheezes has a shape close to a bird's neck, as illustrated in an enlarged part in FIG. 4.

As described above, a plurality of sound types exist in the abnormal breath sounds, and are observed as spectrogram patterns in different shapes depending on the sound types. As is clear from the drawings, the normal breath sounds and the abnormal breath sounds are mixedly detected. The biological sound analyzing apparatus according to the example is configured to perform analysis for dividing the plurality of sound types which are mixed.

<Method of Approximating Breath Sound Signals>

Figure 5:
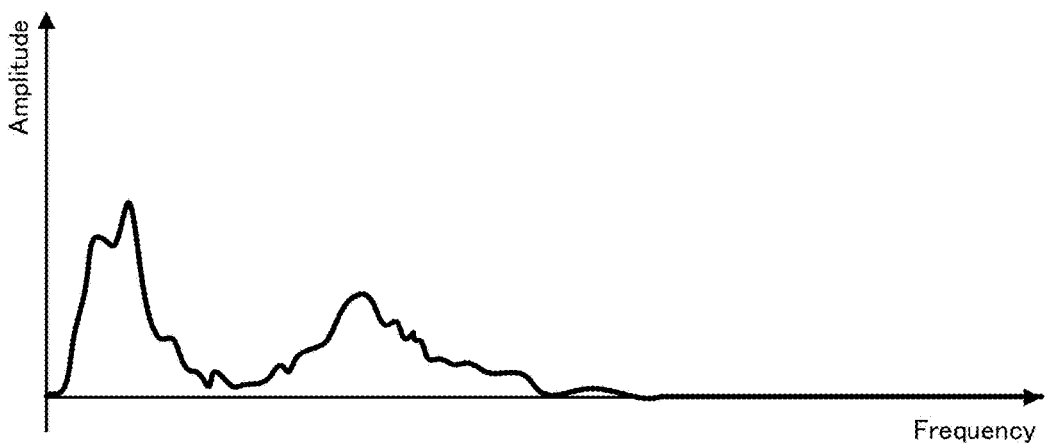
FIG. 5 is a graph illustrating a spectrum in predetermined timing of the breath sounds including the fine crackles.
Figure 6:
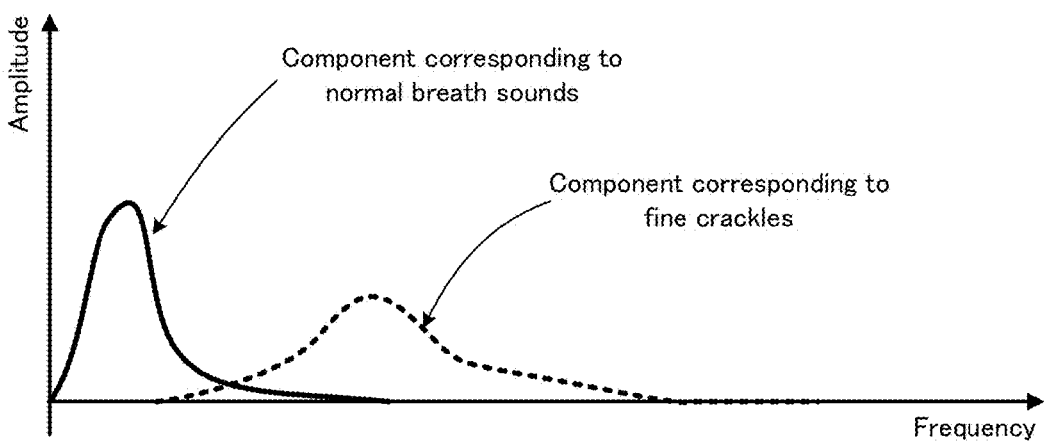
FIG. 6 is a conceptual diagram illustrating a method of approximating the spectrum of the breath sounds including fine crackles.
Figure 7:
FIG. 7 is a graph illustrating a spectrum in predetermined timing of the breath sounds including wheezes.
Figure 8:
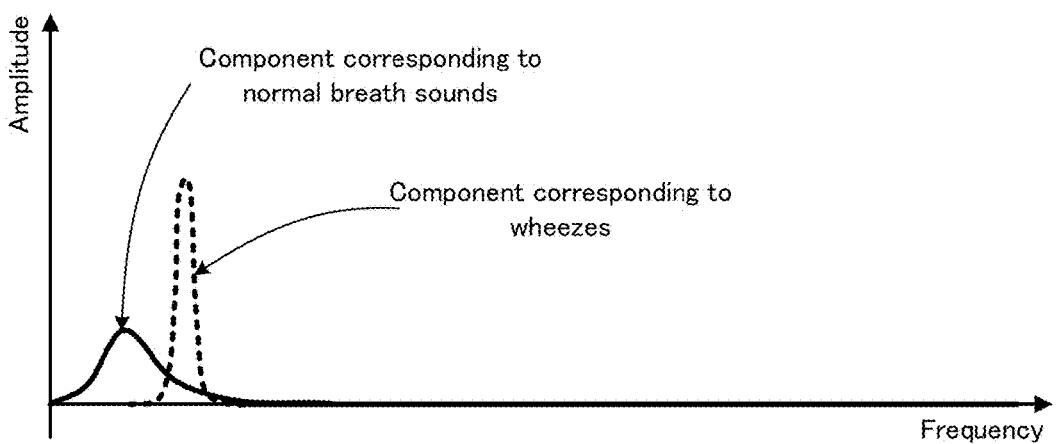
FIG. 8 is a conceptual diagram illustrating a method of approximating the spectrum of the breath sounds including wheezes.

Next, an analyzing method performed by the biological sound analyzing apparatus according to the example will be simply explained with reference to FIG. 5 to FIG. 8. FIG. 5 is a graph illustrating a spectrum in predetermined timing of the breath sounds including the fine crackles. FIG. 6 is a conceptual diagram illustrating a method of approximating the spectrum of the breath sounds including fine crackles. FIG. 7 is a graph illustrating a spectrum in predetermined timing of the breath sounds including wheezes. FIG. 8 is a conceptual diagram illustrating a method of approximating the spectrum of the breath sounds including wheezes.

In FIG. 5, regarding breath sound signals including fine crackles (refer to FIG. 3), if a spectrum is extracted in timing in which the spectrogram pattern corresponding to fine crackles appears strongly, a result illustrated in the drawing is obtained. This spectrum is considered to include normal breath sounds and fine crackles.

In FIG. 6, a spectrum corresponding to normal breath sounds and a spectrum corresponding to fine crackles can be estimated in advance by experiments or the like. Thus, by using the patterns estimated in advance, it is possible to know in what rate a component corresponding to normal breath sounds and a component corresponding to fine crackles are included regarding the aforementioned spectrum.

In FIG. 7, regarding breath sound signals including wheezes (refer to FIG. 4), if a spectrum is extracted in timing in which the spectrogram pattern corresponding to wheezes appears strongly, a result illustrated in the drawing is obtained. This spectrum is considered to include normal breath sounds and wheezes.

In FIG. 8, as in the aforementioned case of normal breath sounds and fine crackles, a spectrum corresponding to wheezes can be also estimated in advance by experiments or the like. Thus, by using the patterns estimated in advance, it is possible to know in what rate a component corresponding to normal breath sounds and a component corresponding to wheezes are included regarding the aforementioned spectrum.

Hereinafter, each process for realizing such analysis will be explained, more specifically.

<Frequency Analysis>

Figures 9, 10:
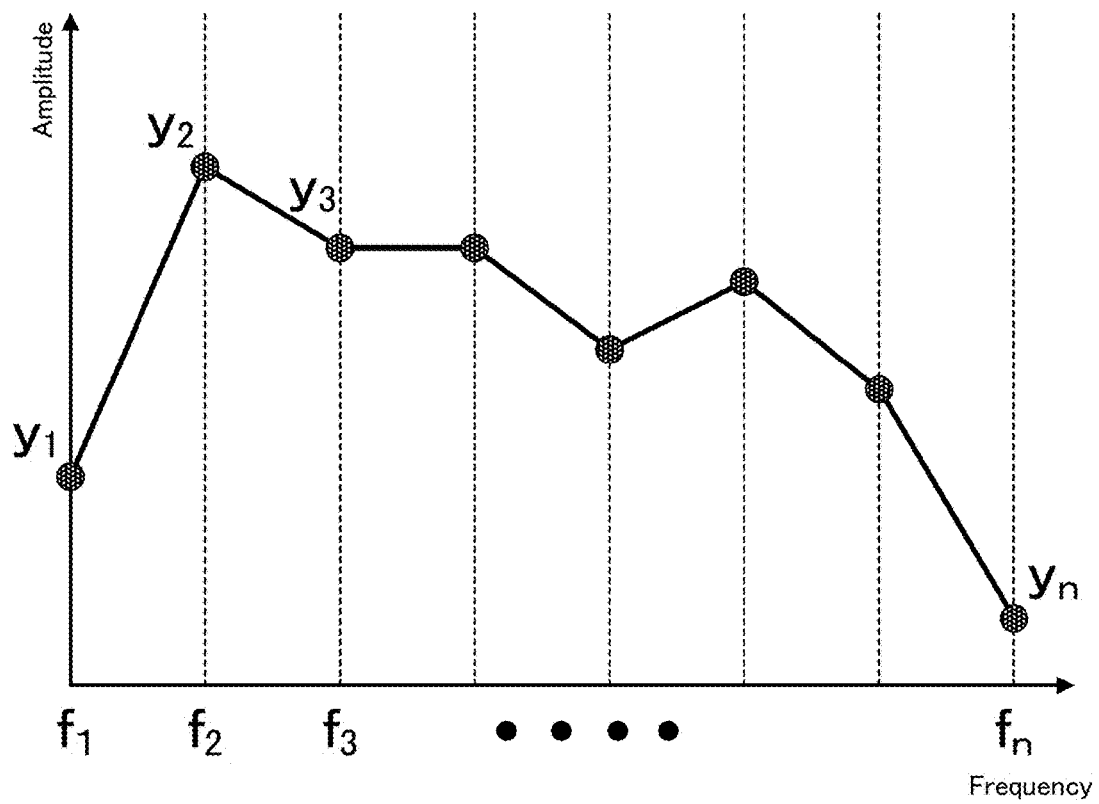
FIG. 9 is a graph illustrating one example of a frequency analyzing method.
FIG. 10 is a graph illustrating one example of a frequency analysis result.
Figure 11:
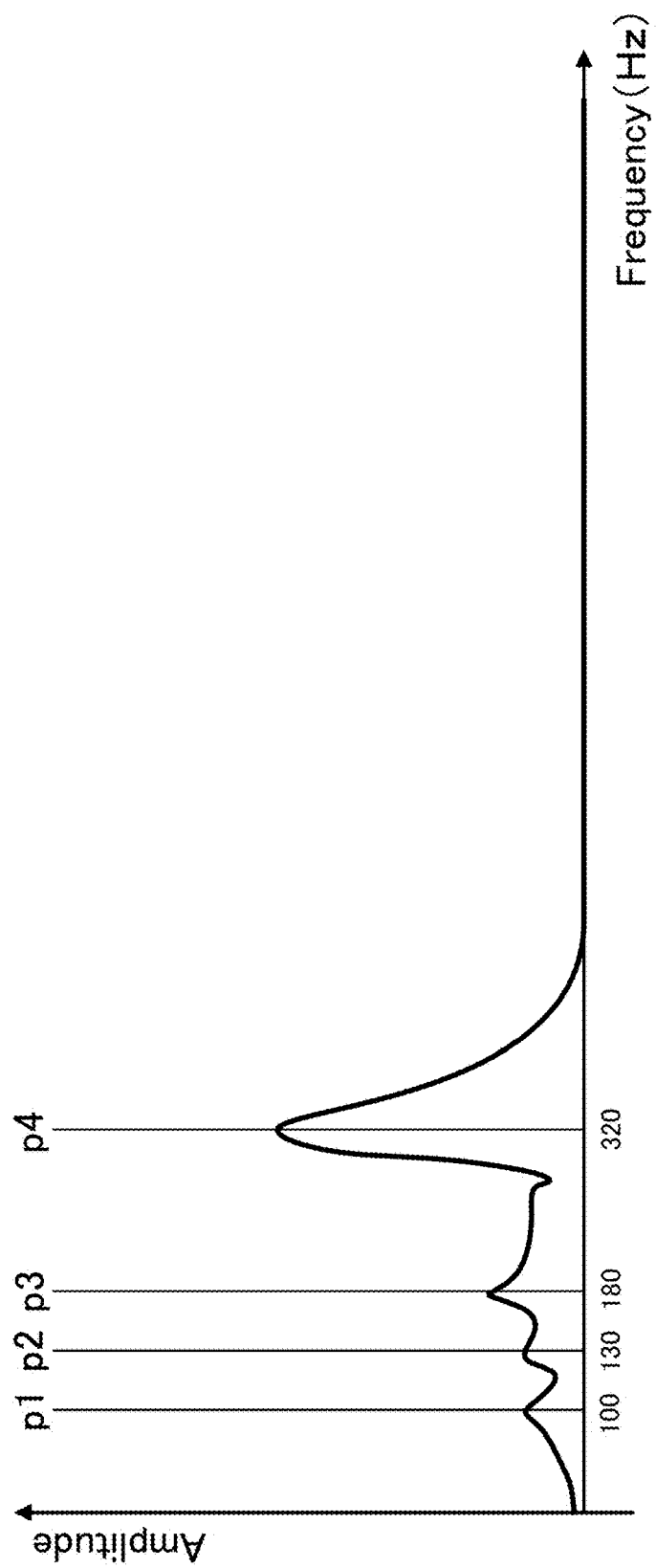
FIG. 11 is a conceptual diagram illustrating a spectrum peak detection result.

The frequency analysis of breath sound signals and the detection of peaks in the analysis result will be explained in detail with reference to FIG. 9 to FIG. 11. FIG. 9 is a graph illustrating one example of a frequency analyzing method. FIG. 10 is a graph illustrating one example of the frequency analysis result. FIG. 11 is a conceptual diagram illustrating a spectrum peak detection result.

In FIG. 9, firstly, the frequency analysis is performed on the obtained breath sound signals. The frequency analysis can be performed by using the existing technology, such as Fast Fourier Transform. In the example, amplitude values at respective frequencies (i.e. amplitude spectrum) are used as the frequency analysis result. A sampling frequency, a window size, a window function (e.g. a Hanning window, etc.) during data acquisition may be determined as occasion demands.

As illustrated in FIG. 10, the frequency analysis result includes n values, wherein "n" is a value determined by the window size or the like in the frequency analysis.

In FIG. 11, the peak detection is performed on the spectrum obtained by the frequency analysis. In an example illustrated in FIG. 11, peaks p1 to p4 are detected at positions 100 Hz, 130 Hz, 180 Hz, and 320 Hz. The peak detection process may be simple because it is only necessary to know at which frequency there is a peak. It is, however, preferable to set a parameter for the peak detection so that even a small peak can be detected.

In the example, a point with a local maximum value is obtained, and then, at most N points (wherein N is a predetermined value) are detected in ascending order from a point with the smallest second-order differential value of the obtained point (i.e. a point with the largest absolute value). The local maximum value is obtained from a point at which a sign of a difference is changed from positive to negative. The second-order differential value is approximated by a difference of the difference. At most N points with the second-order differential value that is less than a predetermined threshold value, which is negative, are selected from a point with the smallest second-order differential value, and position thereof are stored.

<Generation of Basis Set>

Figure 12:
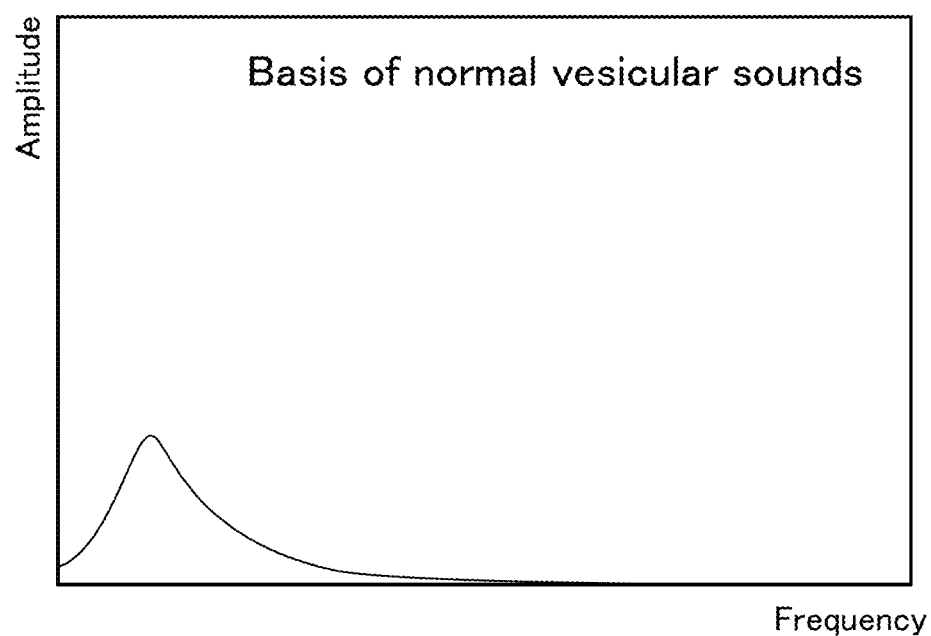
FIG. 12 is a graph illustrating a basis of normal vesicular sounds.
Figure 13:
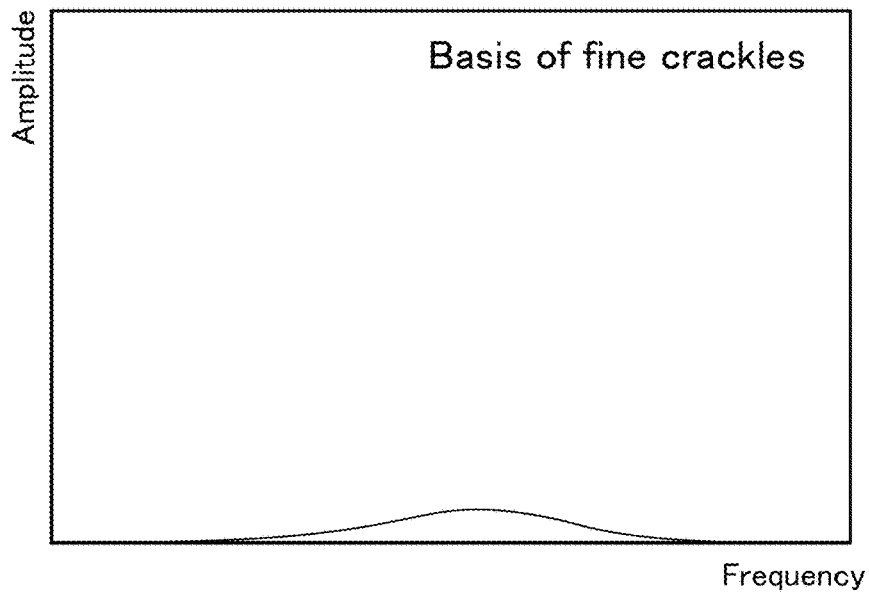
FIG. 13 is a graph illustrating a basis of fine crackles.
Figure 14:
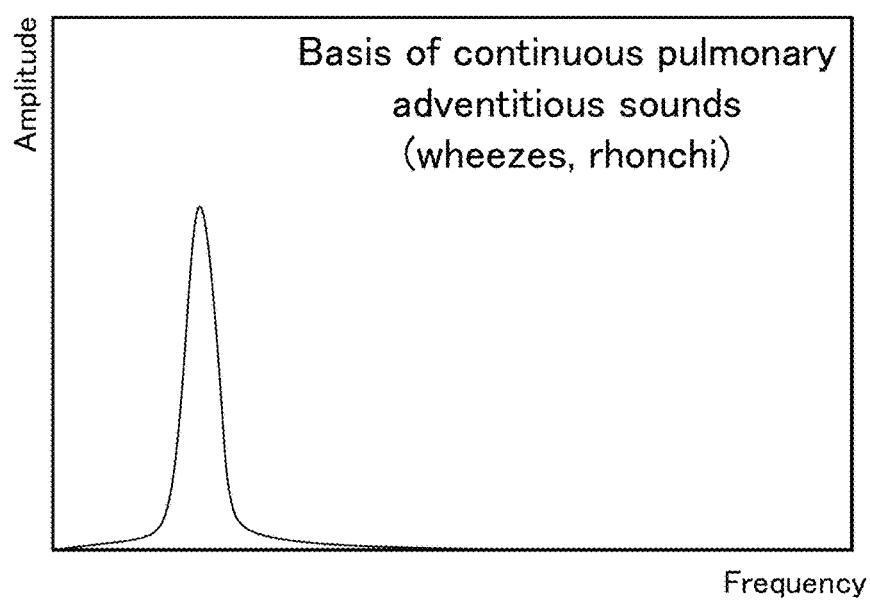
FIG. 14 is a graph illustrating a basis of continuous pulmonary adventitious sounds.
Figure 15:
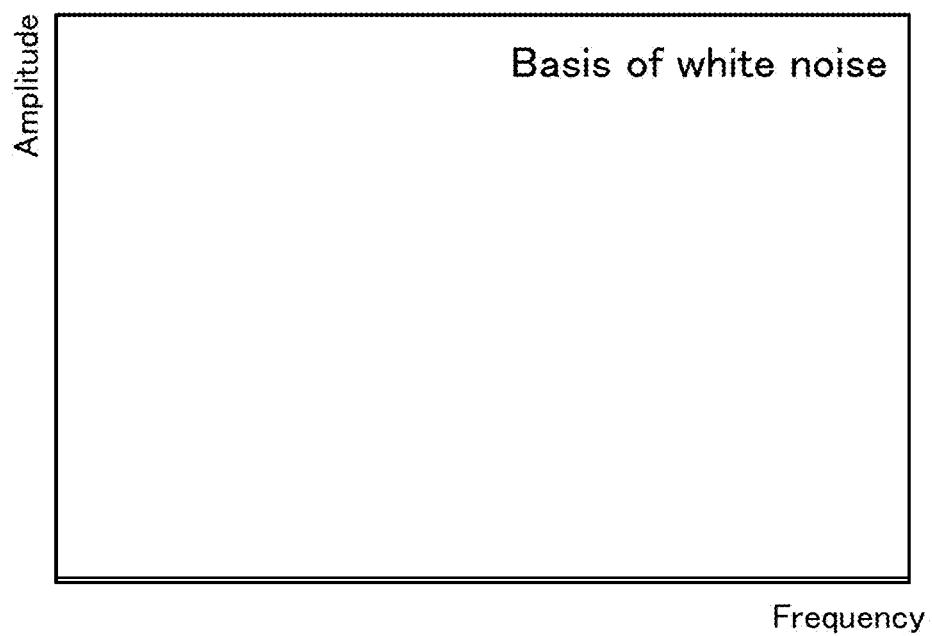
FIG. 15 is a graph illustrating a basis of white noise.
Figure 16A:
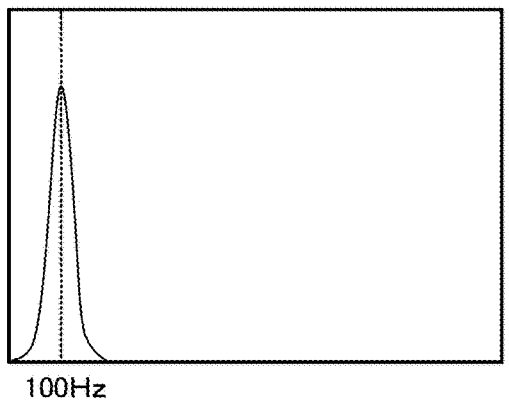
FIG. 16A to FIG. 16D are graph illustrating frequency-shifted bases of continuous pulmonary adventitious sounds.
Figure 16B:
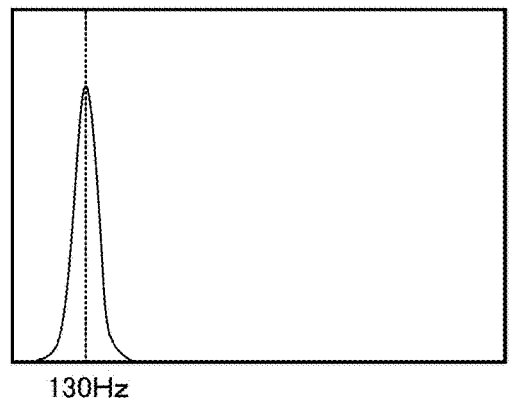
Figure 16C:
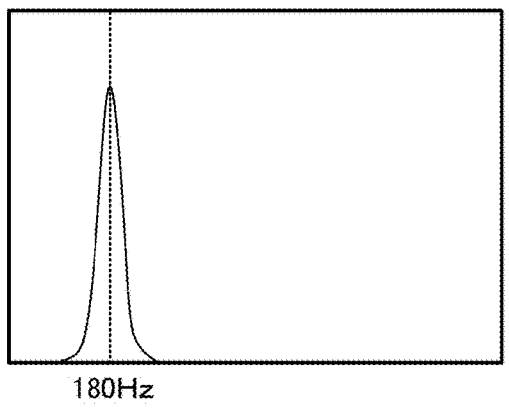
Figure 16D:
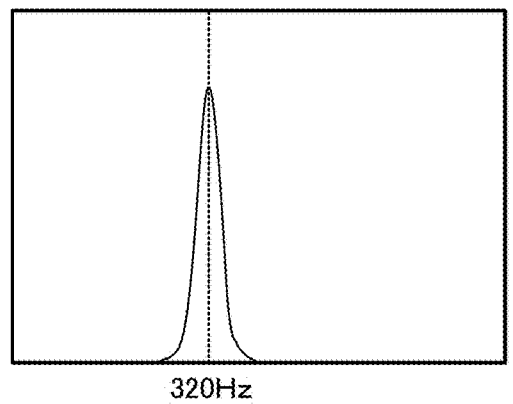

Next, the generation of the basis set will be explained in detail with reference to FIG. 12 to FIG. 16D. FIG. 12 is a graph illustrating a basis of normal vesicular sounds. FIG. 13 is a graph illustrating a basis of fine crackles. FIG. 14 is a graph illustrating a basis of continuous pulmonary adventitious sounds. FIG. 15 is a graph illustrating a basis of white noise. FIG. 16A to FIG. 16D are graphs illustrating frequency-shifted bases of continuous pulmonary adventitious sounds.

As illustrated in FIG. 12 to FIG. 15, each basis corresponding to respective one of the sound types has a particular shape. Each basis includes n numerical values (i.e. amplitude values at respective frequencies), which are the same as the frequency analysis result. Each basis is normalized so that an area, which is surrounded by a line indicating the amplitude value at each frequency and by a frequency axis, has a predetermined value (e.g. 1).

Here, the four bases, which are the basis of normal vesicular sounds, the basis of fine crackles, the basis of continuous pulmonary adventitious sounds, and the basis of white noise, are illustrated; however, the analysis can be performed even if there is only one basis. Moreover, another basis other than the bases exemplified here can be also used. For example, heartbeat sounds and bowel sounds can be analyzed by using bases corresponding to the heartbeat sounds and the bowel sounds, instead of the bases corresponding to the breath sounds exemplified here.

In FIG. 16A to FIG. 16D, the basis corresponding to continuous pulmonary adventitious sounds out of the aforementioned bases is frequency-shifted in accordance with the peak positions detected from the result of the frequency analysis. Here, FIG. 16A to FIG. 16D respectively illustrate examples in which the basis of continuous pulmonary adventitious sounds is frequency-shifted in accordance with the peaks p1 to p4 illustrated in FIG. 11. It is also possible to frequency-shift the bases other than the basis corresponding to continuous pulmonary adventitious sounds.

As a result, the basis set is generated as a set of the basis of normal vesicular sounds, the basis of fine crackles, the bases of continuous pulmonary adventitious sounds, the number of which is the number of the peaks detected, and the basis of white noise.

<Calculation of Coupling Coefficient>

Figure 17:
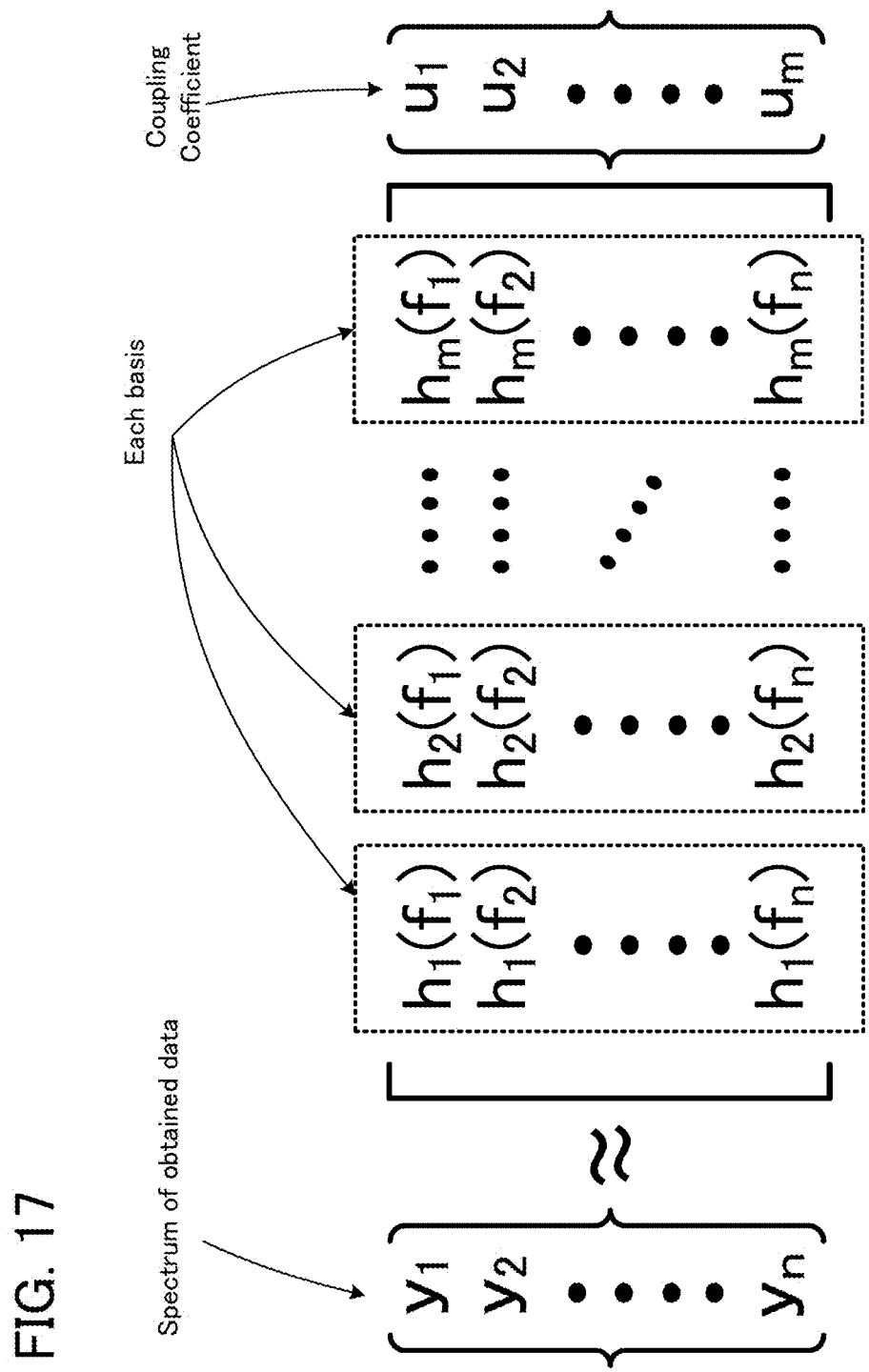
FIG. 17 is a diagram illustrating a relation among a spectrum, each basis, and a coupling coefficient.
Figure 18:
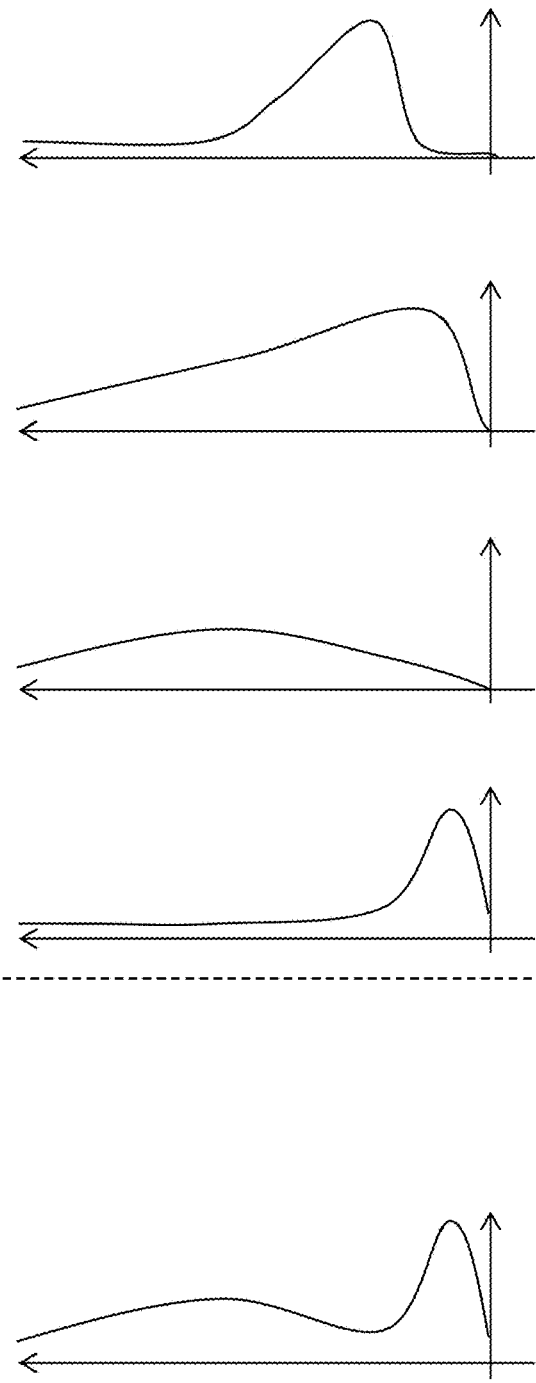
FIG. 18 is a diagram illustrating one example of an observed spectrum and bases used for approximation.
Figure 19:
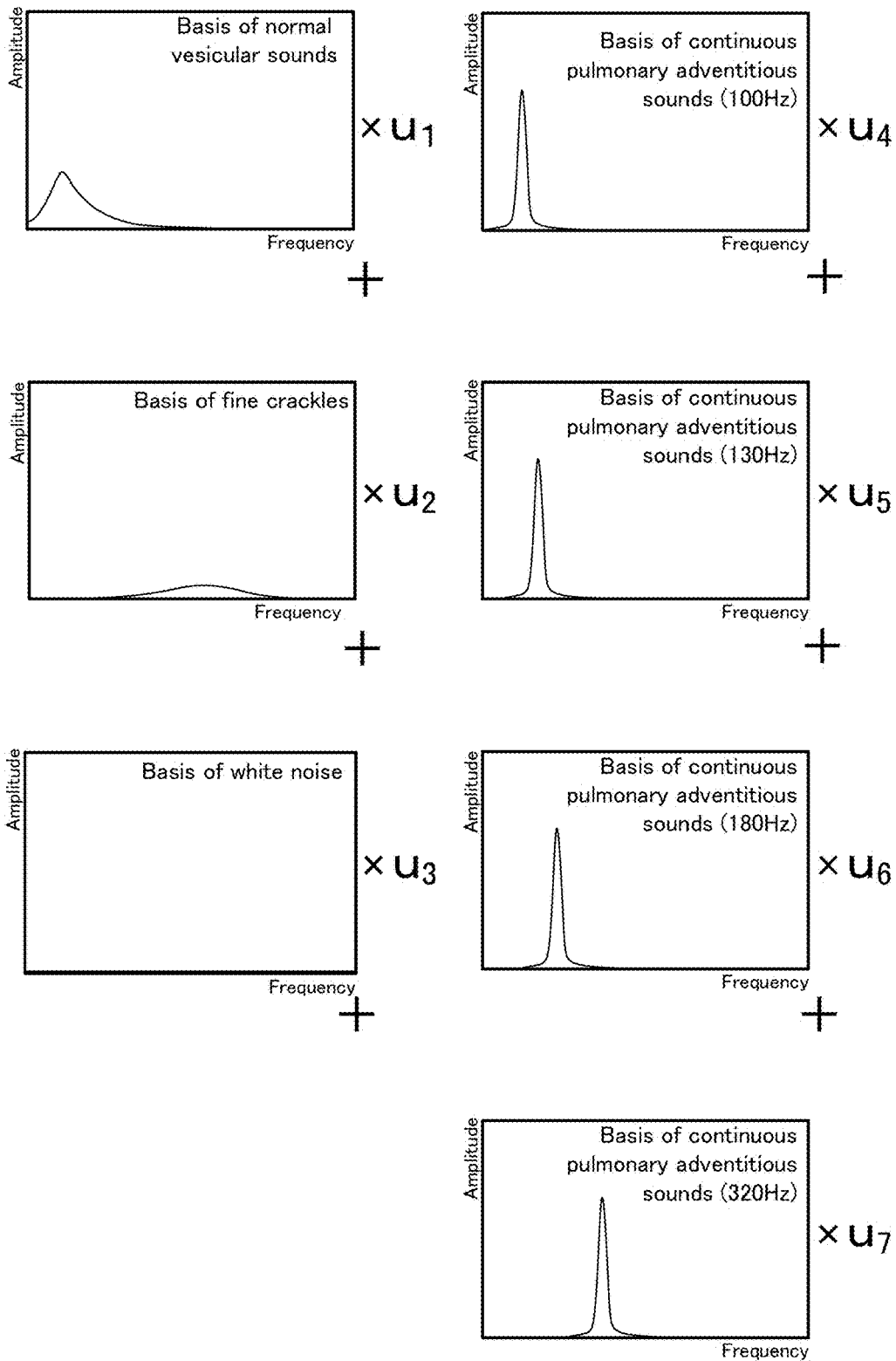
FIG. 19 is diagrams each of which illustrates the coupling coefficient and each basis indicating the spectrum.

Next, the calculation of the coupling coefficient will be explained in detail with reference to FIG. 17 to FIG. 19. FIG. 17 is a diagram illustrating a relation among the spectrum, each basis, and the coupling coefficient. FIG. 18 is a diagram illustrating one example of an observed spectrum and bases used for approximation. FIG. 19 is diagrams illustrating an approximation result by non-negative matrix factorization The relation among a spectrum y, a basis h(f), and a coupling coefficient u, which are to be analyzed, can be expressed in the following equation (1).

[Equation 1]

$$y_i \approx \sum_{k=1}^{m} u_k h_k(f_i) \qquad (1)$$

As illustrated in FIG. 17, the spectrum y and each basis h(f) have n values. On the other hand, the coupling coefficient has m values, wherein "m" is the number of the bases included the basis set.

The biological sound analyzing apparatus according to the example is configured to calculate the coupling coefficient of each of the bases included in the basis set by using non-negative matrix factorization. Specifically, it is only necessary to obtain u that minimizes an optimization criterion function D illustrated in the following equation (2) (wherein each component value of u is non-negative).

[Equation 2]

$$D = \sum_{i=1}^{n} \left( y_i \log \frac{y_i}{\sum_{k=1}^{m} h_k(f_i) u_k} - y_i + \sum_{k=1}^{m} h_k(f_i) u_k \right) \qquad (2)$$

General non-negative matrix factorization is a method of calculating both a basis matrix, which represents a set of basis spectra, and an active matrix, which represents the coupling coefficient. In the example, the basis matrix is fixed, and only the coupling coefficient is calculated.

In order to calculate the coupling coefficient, approximation other than the non-negative matrix factorization may be also used. Even in this case, a desired condition is non-negativity. Hereinafter, a reason for the use of the non-negative approximation will be explained with specific examples.

As illustrated in FIG. 18, it is assumed that an observed spectrum is approximated by four bases A to D to calculate the coupling coefficient. If the non-negativity is a condition, the coupling coefficient u to be expected is 1 correspondingly to the basis A, 1 correspondingly to the basis B, 0 correspondingly to the basis C, and 0 correspondingly to the basis D. In other words, if the non-negativity is a condition, the observed spectrum is approximated to a spectrum obtained by adding the basis A multiplied by 1 and the basis B multiplied by 1.

The coupling coefficient u to be expected if the non-negativity is not a condition is 0 correspondingly to the basis A, 0 correspondingly to the basis B, 1 correspondingly to the basis C, and −0.5 correspondingly to the basis D. In other words, if the non-negativity is not a condition, the observed spectrum is approximated to a spectrum obtained by adding the basis C multiplied by 1 and the basis D multiplied by −0.5.

When the aforementioned two examples are compared, higher approximation accuracy may be obtained if the non-negativity is not a condition, in comparison with a case where the non-negativity is a condition, in some cases. The coupling coefficient u herein, however, represents a component amount of each spectrum, and thus needs to be obtained as a non-negative value. In other words, if the coupling coefficient u is obtained as a negative value, there can be no interpretation as the component amount. In contrast, if the approximation is performed under the non-negativity conditions, the coupling coefficient u corresponding to the component amount can be calculated.

In FIG. 19, the biological sound analyzing apparatus according to the example is configured to calculate the coupling coefficient u by using the basis set including the basis of normal vesicular sounds, the basis of fine crackles, the four bases of continuous pulmonary adventitious sounds, and the basis of white noise, as described above. Thus, the coupling coefficient u is calculated to have seven values $u_1$ to $u_7$.

Here, it may be said that the value $u_1$ corresponding to the basis of normal vesicular sounds is a value indicating a ratio of the normal vesicular sounds to the breath sounds. In the same manner, it may be said that each of the value $u_2$ corresponding to the basis of fine crackles, the value $u_3$ corresponding to the basis of white noise, the value $u_4$ corresponding to the basis of continuous pulmonary adventitious sounds shifted at 100 Hz, the value $u_5$ corresponding to the basis of continuous pulmonary adventitious sounds shifted at 130 Hz, the value $u_6$ corresponding to the basis of continuous pulmonary adventitious sounds shifted at 180 Hz, and the value $u_7$ corresponding to the basis of continuous pulmonary adventitious sounds shifted at 320 Hz is also a value indicating a ratio of each sound type to the breath sounds. Therefore, the signal intensity of each sound type can be calculated from the coupling coefficient.

<Display of Analysis Result>

Figure 20:
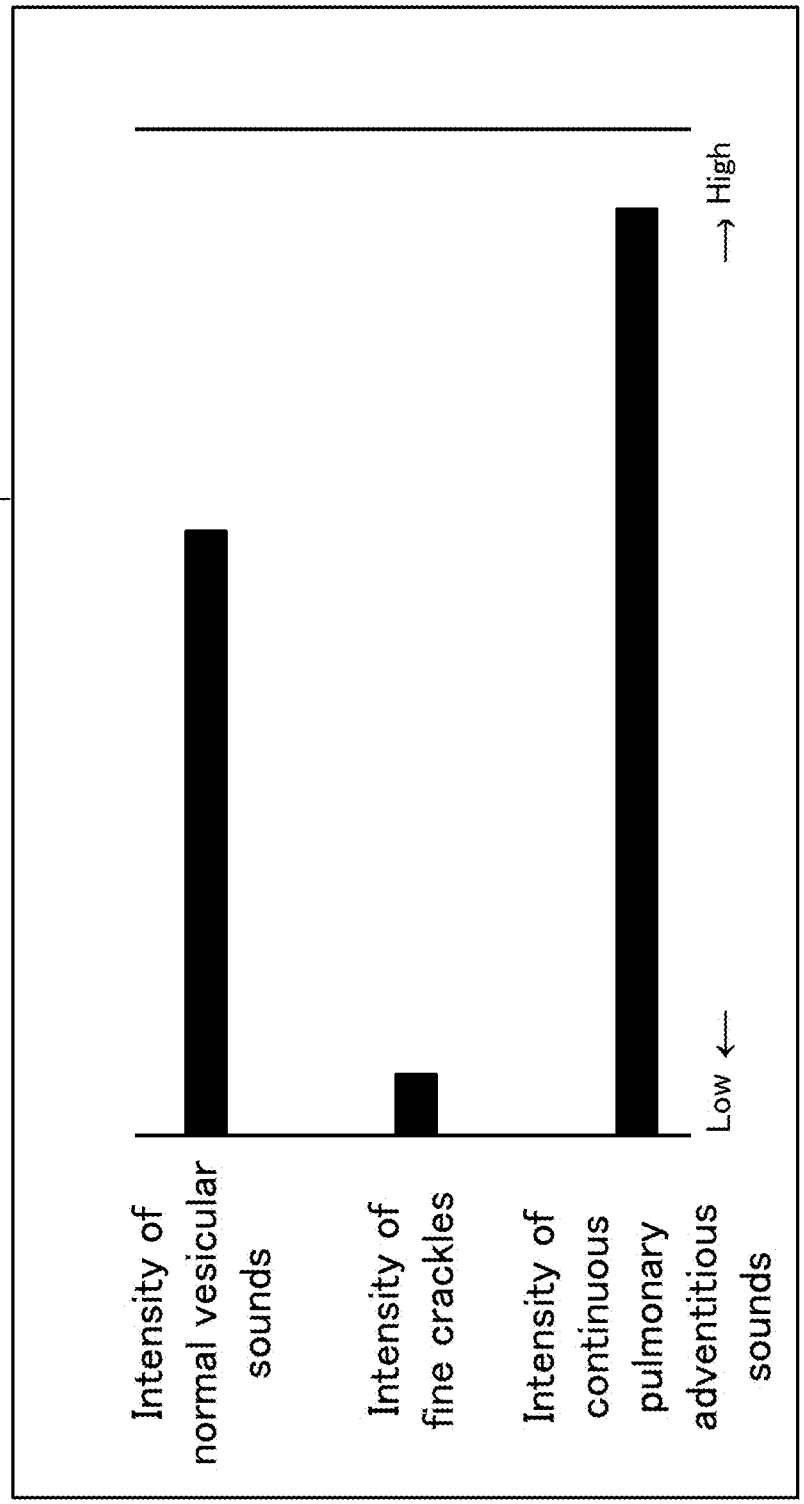
FIG. 20 is a plan view illustrating a display example on a display unit.

Next, the display of the analysis result will be explained in detail with reference to FIG. 20 and FIG. 21. FIG. 20 is a plan view illustrating a display example on the display unit. FIG. 21 is a spectrogram illustrating an example of extraction of wheezes.

As illustrated in FIG. 20, the intensity of each sound type, which is the analysis result, is displayed as a bar graph on a display area 155 of the display unit 150. This display method is one example, and the display may be also performed in another display aspect. For example, a ratio (or content ratio) of each sound type may be calculated and displayed as a pie chart. Alternatively, the intensity of each sound type may be digitized and displayed.

As illustrated in FIG. 21, it is also possible to extract a pattern corresponding to a predetermined sound type from a spectrogram and to display it. Here, there is illustrated the example of the extraction of only a pattern corresponding to wheezes.

Instead of or in addition to the output as the image described above, output by audio data is also possible. Specifically, audio can be outputted separately for each sound type. Alternatively, a particular sound type can be emphasized, and audio can be outputted.

Combination with a method of performing the frequency analysis at certain time intervals, such as Short Time Fourier Transform (STFT), enables dynamic output of the analysis result in each timing.

Moreover, in the example, the signal intensity is calculated as what corresponds to the amplitude spectrum; however, a conversion process may be also performed to correspond to a power spectrum. Moreover, the signal intensity may be converted to a dB value.

The present invention is not limited to the aforementioned embodiments and examples, but various changes may be made, if desired, without departing from the essence or spirit of the invention which can be read from the claims and the entire specification. A biological sound analyzing apparatus, a biological analyzing method, a computer program, and a recording medium that involve such changes are also intended to be within the technical scope of the present invention.

DESCRIPTION OF REFERENCE NUMERALS AND LETTERS 110 biological sound sensor
120 signal memory
125 signal processing unit
130 audio output unit
140 basis holding unit
150 display unit
155 display area
200 processing unit
210 frequency analyzer
220 frequency peak detector
230 basis set generator
240 coupling coefficient calculator
250 signal intensity calculator
260 image generator
y spectrum
h(f) basis
u coupling coefficient

The invention claimed is:

1. A biological sound analyzing apparatus comprising:
a biological sound sensor that obtains signals of biological sounds;
a frequency analyzer operatively connected to an output of the biological sound sensor and configured to obtain information regarding frequency corresponding to predetermined characteristics of a spectrum of biological sounds based on the signals of biological sounds obtained by the biological sound sensor;

a shifter operatively connected to an output of the frequency analyzer and configured to shift a plurality of reference spectrums, which reference spectrums are references for classifying the biological sounds contained in the spectrum of biological sounds, the shifting being in accordance with the information regarding the frequency corresponding to predetermined characteristics of the spectrum of biological sounds, and configured to thereby obtain frequency-shifted reference spectrums;

a calculator that calculates a ratio of each of a plurality of reference spectrums included in the spectrum of biological sounds based on the spectrum of the biological sounds as obtained from the frequency analyzer and the frequency-shifted reference spectrums; and an output device configured to output the calculated ratio of each of the plurality of reference spectrums.

2. The biological sound analyzing apparatus according to claim 1, wherein the biological sounds are breath sounds.

3. The biological sound analyzing apparatus according to claim 2, wherein said outputting device uses non-negative approximation to calculate the ratio of each of the plurality of reference spectrums.

4. The biological sound analyzing apparatus according to claim 2, further comprising a sound separator configured to separate the spectrum of the biological sounds into a plurality of spectrums, each of the plurality of spectrums respectively corresponding to the plurality of reference spectrums.

5. The biological sound analyzing apparatus according to claim 2, wherein the plurality of reference spectrums include reference spectrums corresponding to adventitious sounds.

6. The biological sound analyzing apparatus according to claim 5, wherein said outputting device uses non-negative approximation to calculate the ratio of each of the plurality of reference spectrums.

7. The biological sound analyzing apparatus according to claim 5, further comprising a sound separator configured to separate the spectrum of the biological sounds into a plurality of spectrums, each of the plurality of spectrums respectively corresponding to the plurality of reference spectrums.

8. The biological sound analyzing apparatus according to claim 1, wherein said outputting device uses non-negative approximation to calculate the ratio of each of the plurality of reference spectrums.

9. The biological sound analyzing apparatus according to claim 1, further comprising a sound separator configured to separate the spectrum of the biological sounds into a plurality of image data spectrums, each of the plurality of image data spectrums respectively corresponding to one of the plurality of reference spectrums.

10. A biological sound analyzing method comprising steps of:
obtaining a spectrum of biological sounds;
obtaining information regarding frequency corresponding to predetermined characteristics of the obtained spectrum of biological sounds;
shifting a plurality of reference spectrums, which reference spectrums are references for classifying the biological sounds contained in the spectrum of biological sounds, the shifting being in accordance with the information regarding the frequency corresponding to predetermined characteristics of the spectrum of biological sounds, and thereby obtaining frequency-shifted reference spectrums;
calculating a ratio of each of a plurality of reference spectrums included in the spectrum of biological sounds based on the obtained spectrum of the biological sounds and the frequency-shifted reference spectrums; and
outputting the calculated ratio of each of the plurality of reference spectrums.

11. A non-transitory computer-readable medium on which is stored a program that, upon execution, causes a computer to perform steps of:
obtaining a spectrum of biological sounds;
obtaining information regarding frequency corresponding to predetermined characteristics of the obtained spectrum of biological sounds;
shifting a plurality of reference spectrums, which reference spectrums are references for classifying the biological sounds contained in the spectrum of biological sounds, the shifting being in accordance with the information regarding the frequency corresponding to predetermined characteristics of the spectrum of biological sounds, and thereby and obtaining frequency-shifted reference spectrums;
calculating a ratio of each of a plurality of reference spectrums included in the spectrum of biological sounds based on the obtained spectrum of the biological sounds and the frequency-shifted reference spectrums; and
outputting the calculated ratio of each of the plurality of reference spectrums.

* * * * *